US00PP09206P

United States Patent [19]

Klemm

[11] Patent Number: Plant 9,206

[45] Date of Patent: Jul. 18, 1995

[54] GERANIUM PLANT 'KLEVETTE'

[76] Inventor: Siegfried Klemm, Hanfäcker 8, D 70378 Stuttgart, Germany

[21] Appl. No.: 285,867

[22] Filed: Aug. 4, 1994

[51] Int. Cl.[6] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Arnold, White & Durkee

[57] ABSTRACT

Geranium Klevette is a new and distinct cultivar of germanium, botanically known as *Pelargonium*×*zonale* Hybriden. It is distinguished from other geranium plants by its exceptionally dark purple flowers and a strongly zoned foliage.

1 Drawing Sheet

BACKGROUND OF THE NEW PLANT

Klevette is the product of a controlled breeding program that had the objective of developing plants with the precocity characteristics of PAC Cherry, the cutting production of dark red seedling Cora, and the leaf zonation and flower color of Klefice.

Klevette orignated from the seed parent Marlevit (U.S. Plant Pat. No. 7,908) and pollen parent Klefice (U.S. Plant Pat. No. 6,995). The name Klevette is the name under Breeders Rights protection. Marlevit was originated in the inventor's nursery in 1984 and has been commercially available since 1989. Klefice was discovered as a mutuation, is protected under plant breeders' rights (Plant Protection in Hanover, Germany) and has been commercially available since 1990. Both plants are part of a commerical selection available for purchase and both are trialed and observed each year under indoor and outdoor conditions in the same manner as trials on new varieties. The seed parent Marlevit is protected in Hanover under the tradename Credo and Klefice are also sold under the tradename Arcona. Klevette has not yet been commercialized.

The new cultivar was discovered in 1991 in Stuttgart, Germany and selected by the inventor as one flowering plant from among the progeny of the seed parent Marlevit and the pollen parent Klefice in a controlled environment. The seed from Marlevit was obtained after cultivation of Marlevit with pollen parent Klefice. Klevette differs from both parents in having extremely dark purple flowers and strong zonation.

Compared with the dark red flowers of its seed parent Marlevit, Klevette's flowers are very purple. Neither plant is very well self-branching. Compared to its pollen parent, Klevette has a much darker purple color compared to the bluish dark red or magenta color of Klefice. Klefice is compact and dense with good self-branching zonation, flowers without a summer break, has good precocity and has is a heavily flowering compact plant with a dense canopy because of vigorous vegetative growth and abundant foliage. Similarly, Klevette has foliage with strong zonation but lacks good self-branching leaf characteristics.

The first act of asexual reproduction of Klevette was accomplished when vegetative cuttings were taken from the initial selection in a controlled environment in Stuttgart, Germany by the inventor or technicians working under the supervision of the inventor. Horticultural examination of selected plants demonstrated that the combination of characteristics herein disclosed for Klevette are firmly fixed and are retained through successive generations of asexual reproduction.

Klevette has not be observed under all possible experimental conditions. The phenotype may vary significantly with variations in environment such as temperature, light intensity and day length. The following observations, measurements and comparisons describe plants grown in Stuttgart, Germany under conditions that approximate those used in commerical practice. Similar characteristics are found when the plant is grown under controlled environmental conditions in Germany, Italy and the Netherlands.

Of the many varieties of the same species of geranium plant known to the inventor, the closest resemblance is perhaps to the old Kardinal (a diploid and simple flower plant) or Pelfi Kardino or with Americana Violett. The flower color of the new cultivar appears to be unique and to the inventor's knowledge there are no comparable flower colors in this species of plant. Klevette is not a diploid variety, making Klevette unusual because there are very few tetraploid varieties with this dark purple color.

The plant of this invention is uniquely adapted to a specific slot in the geranium market by its exceptional unusual combination of characteristics such as:

Floral richness which is spectacular due to its unusually colored flowered petals, and the highly double aspect of the individual flowers themselves. This plant virtually continuously exhibits a colorful display of long lasting flowers during the frost-free culture period.

A basally branching compact, but densely foliated, plant of short internodes which has small and heavily zoned attractive leaves and which produces an unusually high proportion of flowers to vegetative growth.

Having non-shattering flowers which are so fully double as to collect moisture and be prone to attendant flower disease problems, but which, when planted in a protected or dry area, produces flower clusters and flowers of exceedingly bright, hot, colorful appearance.

Having a unique flower color which is pleasingly contrasted with tightly bunched, attractively zoned foliage.

Producing individual flowers with a high count of large, wide and heavily imbricated non-fading petals which deliver a burst of color effect not previously seen in this market class of geraniums.

The listed traits in combination offer a plant which is highly attractive and believed will be accepted as exceptional by those skilled in this art for use as a bedding plant or specimen plant, or for use as parent material in future geranium breeding systems.

DESCRIPTION OF THE PHOTOGRAPH

The accompanying color photograph of Klevette illustrates typical inflorescence and leaf characteristics of the new plant. The plant was photographed using professional photographic techniques. The view is taken against a background that illustrates flower color closest to the color values in accordance with The Royal Horticultural Society Colour Chart.

DESCRIPTION OF THE PLANT

The following description uses color references from The Royal Horticultural Society Colour Chart. The color values were determined under prevailing conditions of natural daylight in a greenhouse environment during the month of March in Stuttgart, Germany.

The following traits have been repeatedly observed and are determined to be basic characteristics of Klevette that in combination distinguish this geranium as a new and distinct cultivar. These characteristics include a semi-double dark purple flower, strongly zonated foliage and long-lasting flower clusters.

Classification:

*Botanical.*—*Pelargonium*×*zonale* Hybriden.

*Commercial.*—Klevette, Zonale Geranium.

The plant:

*Form.*—Bush.

*Shape.*—Generally round but not totally uniform.

*Height.*—When marketable — 220–240 mm. End of season — 260–280 mm.

*Time from rooting of cutting to flowering.*—92 days (under commercial greenhouse conditions).

*Pinching to induce branching.*—Not required; this plant is basally branching, but not strongly basally branching.

*Stem length.*—110 mm (indoor). Outdoor — 100–110 mm.

*Internode length.*—12–15 mm.

*Growth rate.*—Medium.

*Leaf stem length.*—45–60 mm.

*Branching character.*—Spreading, with dominant stems forming ponderous lateral outgrowths laden with blooms. One or more lateral branches may be weakly terminally dominant, causing these branches to outgrow remaining lateral breaks.

*Number of stems per stalk.*—3.

*Number of stalks per plant.*—3–4.

*Growth.*—Moderately vigorous, normally much wider than tall.

*Foliage.*—Quantity — A higher than normal canopy density due to the close internode spacing with normal size leaves typical of this species of plant which are cupped to an unusually high degree. Leaf peripheries are lighter than the central lamina portion which highlights the moderately dark or darker zoning. Shape — Kidney shaped or half round. Margin type — Bicrenated. Size — 4.5–5.0 cm length, 7–8 cm width. Texture — Smooth. Color: Upper side — 146A. Under side — 147B. Zonation — 200C in young leaves.

Inflorescence:

*Blooming habit.*—Continuous (April to October. Pinching of old flowers is not required to make new buds appear. Pinching may increase floral richness). Early, no decrease in blooms observed in the fall season.

*Cluster size.*—Medium (measured when more than 20 florets are open). Diameter — 85 mm. Depth — 75 mm.

*Cluster shape.*—Ball-like round shape.

*Petalage.*—7–10.

*Umbels florets.*—Number of flowers per umbel — 70. Size — 45–50 mm. Fullness — Double. Shape — Cup-shaped becoming more flat with maturity. Arrangement — Imbricated. Petal form — Broad. Petal length — Average 2.3 cm. Petal width — Average 1.6 cm. Margin type — Entire. Petal persistence — 7 days if not pollinated. Texture — Soft. Appearance — Velvety.

*Color.*—Outer petal/floret: Body — Mixture of 74A and 66A and dark red. Center is orange, but not conspicuous because of the filling of the flowers. An orange powder is seen on petals if flowers are opened by hand. The basal portions of the claw portion of the petals and petaloids is white. Base — There is no RHS color card for this color. Reverse side — 67A/66A. Inside petal/floret: Body — Mixture of 74A/66A/dark red/dark center. Base — No RHS color card for this color. Reverse side — 67A/66A.

Petaloids.—Number — 1–4. Size — 6–12 mm. Length, 4–6 mm width. Color — 66A with orange.

*Pedicel posture.*—Ascending with the opening of flowers, but standing hemispherically around the apex of the peduncle when all florets are in full bloom.

*Pedicel thickness.*—Similar to that of the species and sufficiently strong to position flowers as they open.

*Pedicel length.*—19–20 mm.

*Pedicel color.*—Light brown (color is visible before the flowers open).

*Pedicel arrangement.*—Radiate from the apex of the peduncle as typical of most members of the species.

*Discoloration after full bloom.*—Mature flowers become darker but do not fade.

*Weather resistance.*—The double flowers of this plant may be compressed by adjacent flowers of the tight cluster to retain a cup shape which will capture and retain rain droplets. The highly imbricated petals prevent drainage thereof. Unless such moisture is removed by shaking or wind, flowers may be susceptible to botrytus.

*Persistence.*—In dry weather, clusters will normally hang on and dry. If no fertilization has taken place the peduncle will abscise with dried flowers intact.

*Disease resistance.*—Except as noted above, the disease resistance of this plant has not been systematically observed.

*Fragrance.*—None.

*Lasting quality.*—On plant — More than 23 days. Cut flower — 7 days.

Lasting quality is observed by determining how long flowering clusters maintain appearance without picking off old florets. Additionally, the number of days observed for the time it takes from the day when the first floret is open to the day when the last floret opens. This time depends on the number of florets found in one cluster and this number with geraniums generally varies from 20 to more than 70. Information on lasting quality is provided in terms of how long flowering clusters maintain appearance without picking off old florets.

Bud:

*Average diameter.*—11 mm.

*Average depth.*—12 mm.

*Shape.*—Only the sepals are pointed; the tightly massed unexpanded petals form a truncated assemblage with a blunt apex.

*Rate of opening.*—Somewhat slower than average because of filling.

*Color of petals.*—When sepals first divide — Grayish purple. When petals begin to unfurl — Deep purple.

Sepals:

*Shape.*—Long and pointed.

*Number.*—5.

*Opened flowers.*—Sepals splay to a relaxed position.

*Color.*—Inside — b 144A. Outside — 145A (when buds are very young).

*Number of buds and flowering clusters appearing at the same time.*—Early Stage (young and marketable) — One bud (upon the leaves) and one flowering cluster. Middle (number of clusters appearing in greenhouse up until the middle of May) — Approximately 3 matured clusters picked off from the date of marketability to the middle of May when plants are placed outdoors. Late (middle of May to end of September) — Approximately 65.

Reproductive organs:

*Perfect.*—Yes (contain both pistils and stamens but stamens look degenerated and deformed. Some do not have anthers and bring pollen).

*Stamens.*—Number — 6–7 (not all fertile) arranged around the ovaries. Anthers: Size — 1.8 mm. Color — Yellow. Filaments (threads): Length — 6 mm. Color — Pink.

*Pollen.*—Color — Orange.

*Pistils.*—Number — 1 with 5–6 branches (stigmas) Styles: Length — 9 mm. Color — Green/dark red. Stigmas: Color — Dark red.

*Fruit.*—Fertile — Yes. Color — Green later becoming sand colored. Length of seed — 3–4.5 mm. Color of seed — Brown.

What is claimed is:

1. A new distinct geranium cultivar, substantially as herein described and shown, characterized by its exceptionally dark purple flowers.

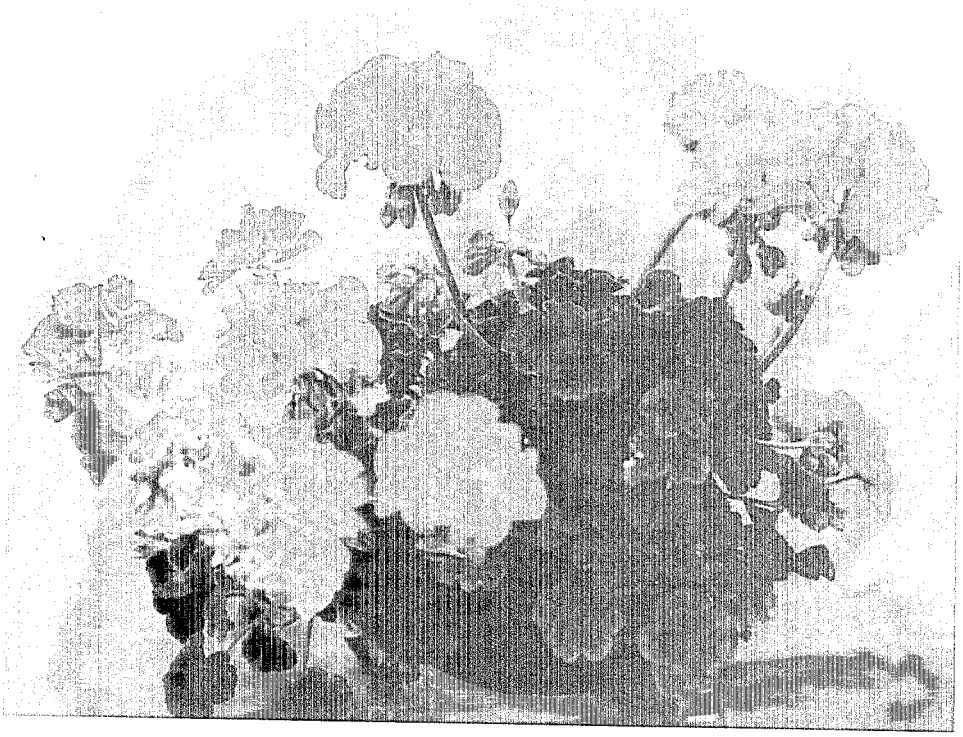

* * * * *